United States Patent [19]
Li et al.

[11] Patent Number: 5,735,903
[45] Date of Patent: Apr. 7, 1998

[54] MENISCAL AUGMENTATION DEVICE

[76] Inventors: Shu-Tung Li, 1 Kiowa Ter., Oakland, N.J. 07436; Kevin R. Stone, 1 Throckmorton La., Mill Valley, Calif. 94941

[21] Appl. No.: 457,971

[22] Filed: Jun. 1, 1995

Related U.S. Application Data

[60] Division of Ser. No. 250,008, May 27, 1994, which is a continuation-in-part of Ser. No. 232,243, Apr. 25, 1994, Pat. No. 5,624,463, which is a continuation-in-part of Ser. No. 809,003, Dec. 17, 1991, Pat. No. 5,306,311, which is a continuation-in-part of Ser. No. 520,027, May 7, 1990, Pat. No. 5,108,438, which is a continuation-in-part of Ser. No. 317,951, Mar. 2, 1989, Pat. No. 5,007,934, which is a continuation-in-part of Ser. No. 75,352, Jul. 20, 1987, Pat. No. 4,880,429.

[51] Int. Cl.$^6$ ............................................. A61F 2/38
[52] U.S. Cl. ........................... 623/20; 623/16; 623/66
[58] Field of Search ............................. 623/1, 11, 12, 623/16, 18, 266, 20; 424/422, 423, 424

[56] References Cited

U.S. PATENT DOCUMENTS

| | | | |
|---|---|---|---|
| 3,443,261 | 5/1969 | Battista | 3/1 |
| 3,551,560 | 12/1970 | Thiele | 424/95 |
| 3,855,638 | 12/1974 | Pilliar | 3/1 |
| 4,000,525 | 1/1977 | Klawitter et al. | 3/1.911 |
| 4,055,862 | 11/1977 | Farling | 3/1.91 |
| 4,060,081 | 11/1977 | Yannas et al. | 128/156 |
| 4,064,567 | 12/1977 | Burstein et al. | 3/1.91 |
| 4,085,466 | 4/1978 | Goodfellow et al. | 3/1.91 |
| 4,280,954 | 7/1981 | Yannas et al. | 260/123.7 |
| 4,291,013 | 9/1981 | Wahlig et al. | 424/16 |
| 4,344,193 | 8/1982 | Kenney | 3/1.911 |
| 4,350,629 | 9/1982 | Yannas et al. | 260/123.7 |
| 4,351,069 | 9/1982 | Ballintyn et al. | 3/1.912 |
| 4,378,224 | 3/1983 | Nimni et al. | 8/94.11 |
| 4,385,404 | 5/1983 | Sulley et al. | 3/1.91 |
| 4,400,833 | 8/1983 | Kurland | 3/1 |

(List continued on next page.)

FOREIGN PATENT DOCUMENTS

| | | |
|---|---|---|
| 1 170 001 | 9/1995 | Canada. |
| 0 277 678 | 8/1988 | European Pat. Off.. |
| 1 515 963 | 7/1976 | United Kingdom. |
| 83/03536 | 10/1983 | WIPO. |

OTHER PUBLICATIONS

Smillie (1943) *The British Journal of Surgery*, Meeting of the British Orthopedic Association, pp. 398–401.
Bullough et al. (1970) *J. Bone Joint Surg.* 52B:564–570.
Cox and Cordell (1977) *Clin. Orthopaed. Related Res.* 125:236–242.
Seedhom (1979) *Engin. Med.* 8:207–219.
Seedhom and Hargreaves (1979) *Engin. Med.* 8:220–228.
Arnoczky and Warren (1983) *J. Sports Med.* 11:131–141.
Arnoczky, *Advances In Orthopaedic Surgery*, the Williams and Wilkins Co., (1984) Baltimore/London, pp. 244–252.
Anderson *Grant's Atlas of Anatomy* (8th Ed.) Williams and Wilkins Co., (1984) Baltimore/London, sections 4–56, 4–57, 4–60, and 4–61.
Arnoczky et al. (1986) 32nd Annual ORS, New Orleans, Louisiana.
Leenslag et al. *Biological and Biomechanical Performance of Biomaterials* (Christel et al., eds.) Elsevier Science Publishers B.V., Amsterdam, (1986), pp. 147–152.
Milachowski et al. (1986) *Orthopadischem Klinik, Klinikum Grosshadern*, Munchen. z. Orhop. (Jul. –Aug. 1986) 124:508–512.
Ahmed (19 ) "Load–Carrying Characteristics of Meniscus and Tibial Plateau –a Review of Recent Results".
Beaupre et al. (1986) *Clin. Ortho. and Rel. Res.* 208:72–75.

*Primary Examiner*—David Isabella
*Attorney, Agent, or Firm*—Fish & Richardson P.C.

[57] ABSTRACT

The present invention relates to a meniscal augmentation device of biocompatible and at least partially bioresorbable fibers for implantation into a segmental defect of a meniscus in a subject. Upon implantation, the composite of the device and the meniscus establishes a scaffold adapted for ingrowth of meniscal fibrochondrocytes. The invention further pertains to methods of fabricating and using the device.

12 Claims, 7 Drawing Sheets

U.S. PATENT DOCUMENTS

| | | | |
|---|---|---|---|
| 4,418,691 | 12/1983 | Yannas et al. | 128/156 |
| 4,448,718 | 5/1984 | Yannas et al. | 260/123.7 |
| 4,458,678 | 7/1984 | Yannas et al. | 128/155 |
| 4,472,840 | 9/1984 | Jefferies | 3/1.9 |
| 4,502,161 | 3/1985 | Wall | 3/1.91 |
| 4,505,266 | 3/1985 | Yannas et al. | 128/1 R |
| 4,542,539 | 9/1985 | Rowe, Jr. et al. | 623/16 |
| 4,544,516 | 10/1985 | Hughes et al. | 264/108 |
| 4,578,079 | 3/1986 | Ruoslahti et al. | 623/11 |
| 4,589,881 | 5/1986 | Pierschbacher et al. | 623/11 |
| 4,614,794 | 9/1986 | Easton et al. | 530/356 |
| 4,627,853 | 12/1986 | Campbell et al. | 623/16 |
| 4,661,111 | 4/1987 | Ruoslahati et al. | 623/11 |
| 4,789,663 | 12/1988 | Wallace et al. | 623/16 |
| 4,801,299 | 1/1989 | Bendel et al. | 623/1 |
| 5,007,934 | 4/1991 | Stone | 623/20 |
| 5,116,374 | 5/1992 | Stone | 623/16 |
| 5,158,574 | 10/1992 | Stone | 623/66 |

… 1

MENISCAL AUGMENTATION DEVICE

CROSS-REFERENCE TO RELATED APPLICATIONS

This is a divisional of copending application Ser. No. 08/250,008, filed May 27, 1994, which is a continuation-in-part application of U.S. Ser. No. 08/232,743 filed Apr. 25, 1994, now U.S. Pat. No. 5,624,243 which is a continuation-in-part of U.S. Ser. No. 07/809,003, filed Dec. 17, 1991, which is a continuation-in-part application of U.S. Ser. No. 07/520,027, filed May 7, 1990, now U.S. Pat. No. 5,108,438, which, in turn, is a continuation-in-part application of U.S. Ser. No. 07/317,951, filed Mar. 2, 1989, now U.S. Pat. No. 5,007,934, which is a continuation-in-part application of U.S. Ser. No. 07/075,352, filed Jul. 20, 1987, now U.S. Pat. No. 4,880,429.

FIELD OF THE INVENTION

The present invention relates to implantable prosthetic devices, and more particularly, is directed to the regeneration of meniscal tissue using meniscal augmentation devices and in vivo scaffolds.

BACKGROUND OF THE INVENTION

The medial and lateral menisci are biconcave, generally C-shaped wedges of fibrocartilage interposed between the condyles of the femur and the tibia. Together, the menisci act as crucial stabilizers, providing a mechanism for force distribution, and a lubricant between the tibia and the femur. Without functional menisci, stress concentration occurs in the knee in conjunction with abnormal joint mechanics. These phenomena can result in premature development of arthritis.

In the past, the treatment of choice for injured or diseased menisci was partial or complete excision or replacement of the meniscus. Unfortunately, meniscectomy is often followed by degenerative changes within the knee joint. Replacement of injured menisci in an otherwise healthy knee joint, however, may prevent arthritic changes and may stabilize the joint. In diseased joints, replacement of the meniscus may reduce the progression of the disease process. Allografting or meniscal transplantation have been performed in dogs and humans. However, these approaches have been only partially successful over the long term due to the host's immunologic response to the graft, failures in the cryopreservation process, and failures of the attachment sites.

Menisci have also been replaced by prostheses composed of permanent artificial material. Such prostheses have been constructed of purely artificial materials in order to minimize the possibility of an immunological response thereto. The use of such artificial materials is believed to be advantageous because it permits construction of a structure which can withstand the high and repeated loads which are encountered in the knee joint, and because it can alter the joint mechanics in beneficial ways that biological materials supposedly would not tolerate.

For example, a Teflon® net has been used to replace the resected meniscus of a dog upon which fibrous ingrowth or regeneration was observed, although accompanied by significant chondral abrasion. Resilient materials such as silicone rubber or Teflon® with reinforcing stainless steel or nylon strands have also been employed in the construction of prosthetic menisci (U.S. Pat. No. 4,502,161). Meniscal components have also been generated from resilient plastic materials (U.S. Pat. No. 4,085,466). In addition, reconstruction of menisci following lesioning has been attempted with carbon-fiber-polyurethane-poly (L-lactide) with some success (Leeslag et al. (1986) *Biological and Biomechanical Performance of Biomaterials* (Christel et al., eds.) Elsevier Science Publishers B.V., Amsterdam, pp. 341–352).

The replacement of meniscal tissue with structures consisting of permanent artificial materials, however, has generally been unsuccessful. This lack of success is due principally to the fact that opposing articular cartilage of human and animal knee joints is fragile. The articular cartilage in the knee joint will not withstand abrasive interfaces, nor compliance variances from normal, which eventually result from implanted artificial prosthetic menisci. In addition, joint forces are multiples of body weight which, in the case of the knee and hip, are typically encountered over a million cycles per year. Thus far, permanent artificial menisci have not been composed of materials having natural meniscal properties, nor have they been able to be positioned securely enough to withstand such routine forces.

Stone (U.S. Pat. Nos. 5,007,934, 5,116,374, and 5,158,574) describes a prosthetic, resorbable meniscus comprising biocompatible and bioresorbable fibers, such as natural polymers, and methods for fabricating such prosthetic menisci. In addition, Stone describes methods of regenerating meniscal tissue by implanting the resorbable prosthetic meniscus into a human knee.

SUMMARY OF THE INVENTION

The present invention pertains to a meniscal augmentation device for implantation into a segmental defect of a meniscus in a subject. Upon implantation into the segmental defect of a meniscus, the composite formed by the meniscus and the device has an in vivo outer surface contour substantially the same as a natural meniscus without a segmental defect, and establishes a biocompatible and an at least partially bioresorbable scaffold adapted for ingrowth of meniscal fibrochondrocytes. The scaffold, together with the ingrown meniscal fibrochondrocytes support natural meniscal load forces.

A "segmental meniscal defect" as used herein encompasses a tear or lesion (including radial tears, horizontal tears, bucket handle tears, complex tears) in less than the entire meniscus, resulting in partial resection of the meniscus. The meniscal augmentation device is composed of biocompatible and at least partially bioresorbable fibers, such as natural polymers, and has an outer surface contour substantially complementary to the segmental defect of the meniscus.

The present invention also pertains to methods for fabricating a meniscal augmentation device having in vivo the shape of a segmental defect in a meniscus. The method involves placing a plurality of biocompatible and bioresorbable fibers into a mold defining the shape of the segmental defect, lyophilizing the fibers, and contacting the fibers with a chemical crosslinking agent such that the fibers assume the shape of the mold. The mold defines the outer surface of the device to complement the segmental defect. Alternatively, after the molding is completed, the structure or matrix formed in the mold is cut so that its outer surface is complementary to the segmental defect. This method yields a dry, porous volume matrix adapted to have an outer surface contour complementary to that of the segmental defect in the meniscus. When implanted into the segmental defect of the meniscus, the matrix establishes a biocompatible and an at least partially bioresorbable scaffold for ingrowth of meniscal fibrochondrocytes and for supporting natural meniscal load forces. The in vivo outer surface of the composite of the meniscus and the implanted matrix is substantially the same as that of a natural meniscus without segmental defect.

In addition, the present invention provides a method for regenerating meniscal tissue in vivo. The method involves fabricating a meniscal augmentation device composed of biocompatible and at least partially bioresorbable fibers as described above, and then implanting the device into a segmental defect in the meniscus. This implanted device establishes a biocompatible and an at least partially bioresorbable scaffold adapted for ingrowth of meniscal fibrochondrocytes. The scaffold in combination with the ingrown meniscal fibrochondrocytes support natural meniscal load forces.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

Figure 1:
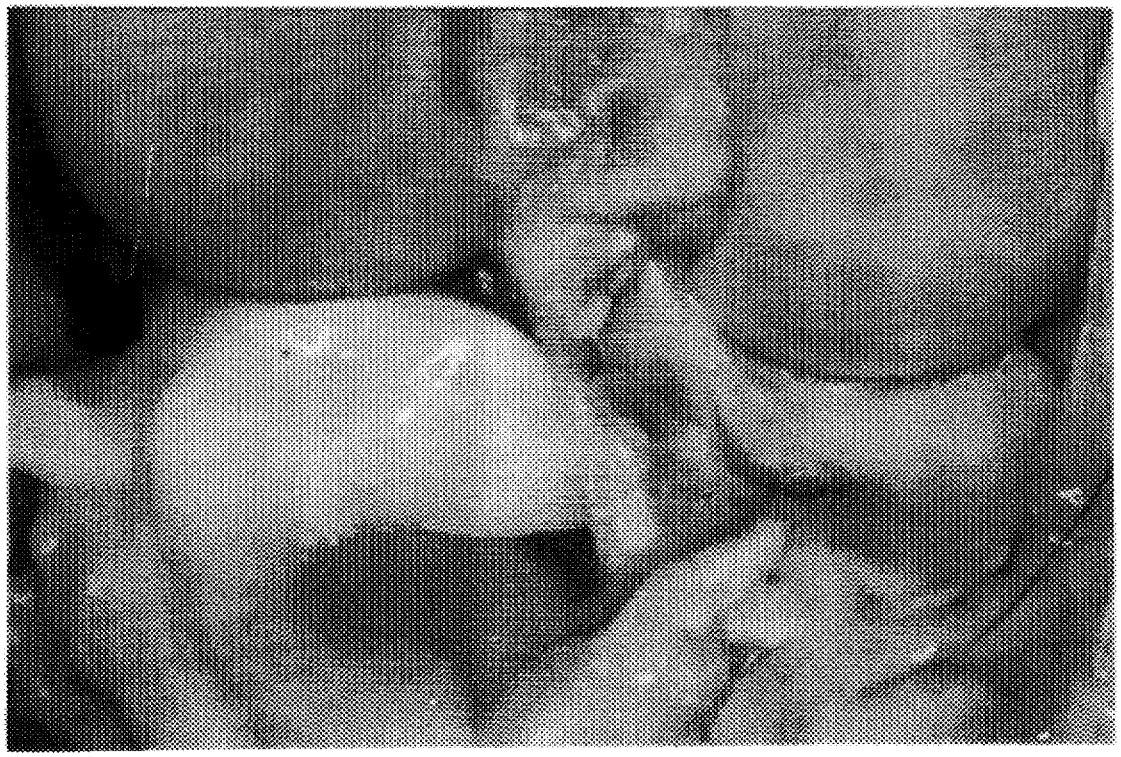
FIG. 1 is a photographic representation of a human knee joint with intact menisci.
Figure 2:
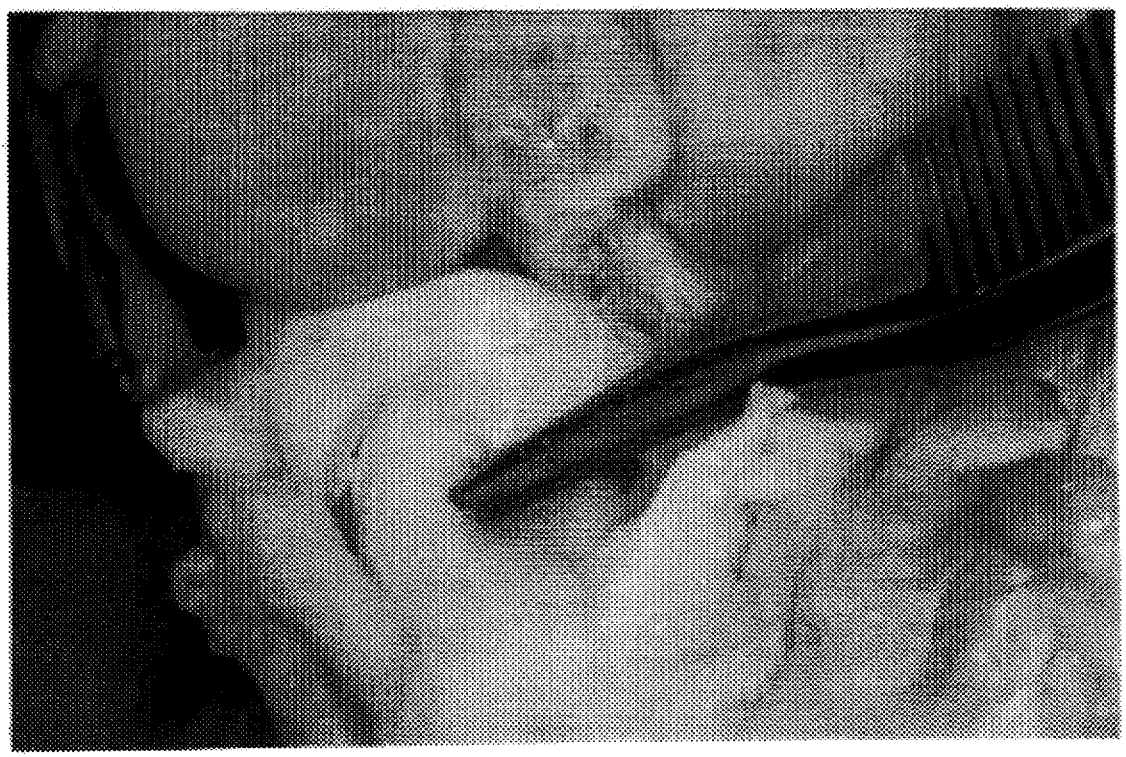
FIG. 2 is a photographic representation of a human knee joint with a meniscus displaying segmental defects.
Figure 3:
FIG. 3 is a photographic representation of a human knee joint with a meniscus displaying segmental defects.
Figure 4:
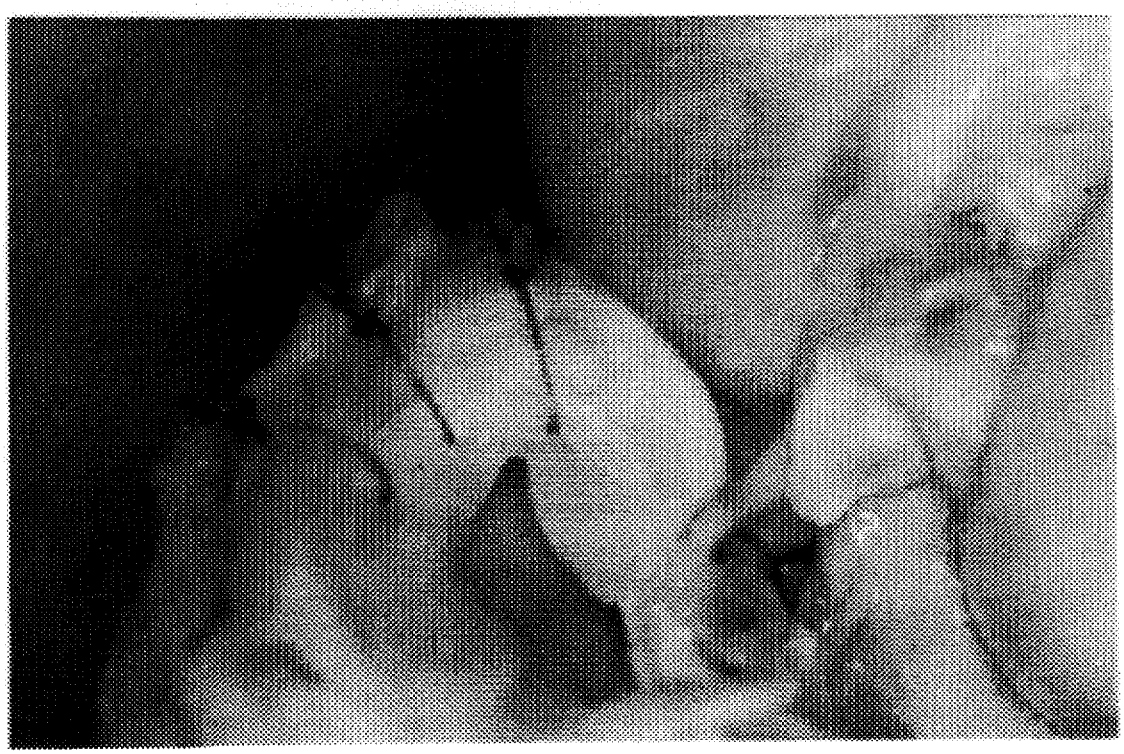
FIG. 4 is a photographic representation of a meniscal augmentation device sutured into a segmental defect in a meniscus.
Figure 5:
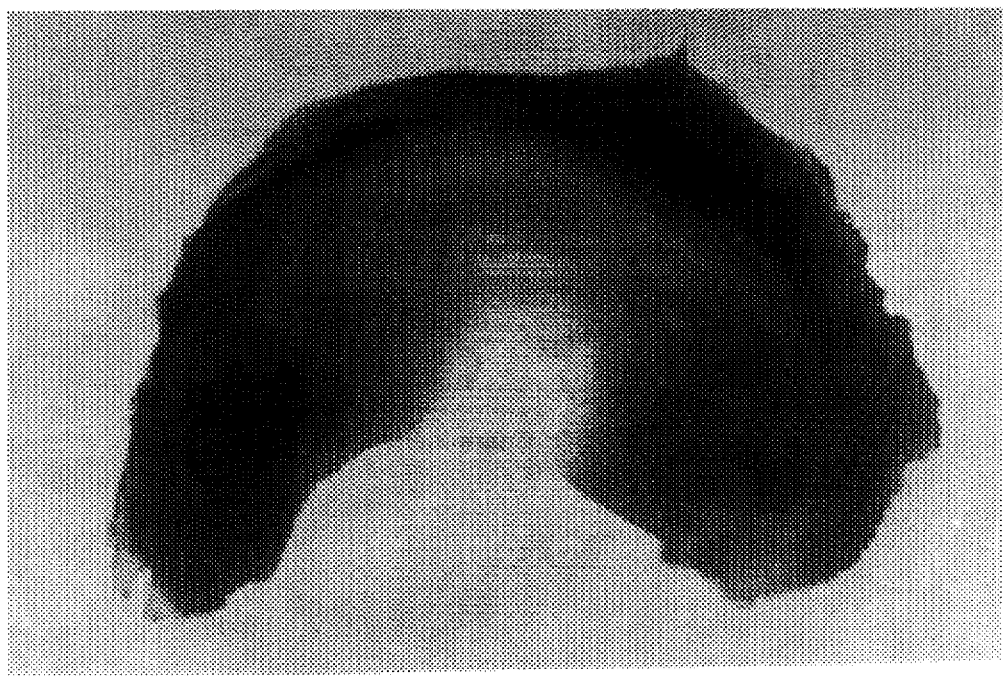
FIG. 5 is a photographic representation of menisci with segmental defects.
Figure 6:
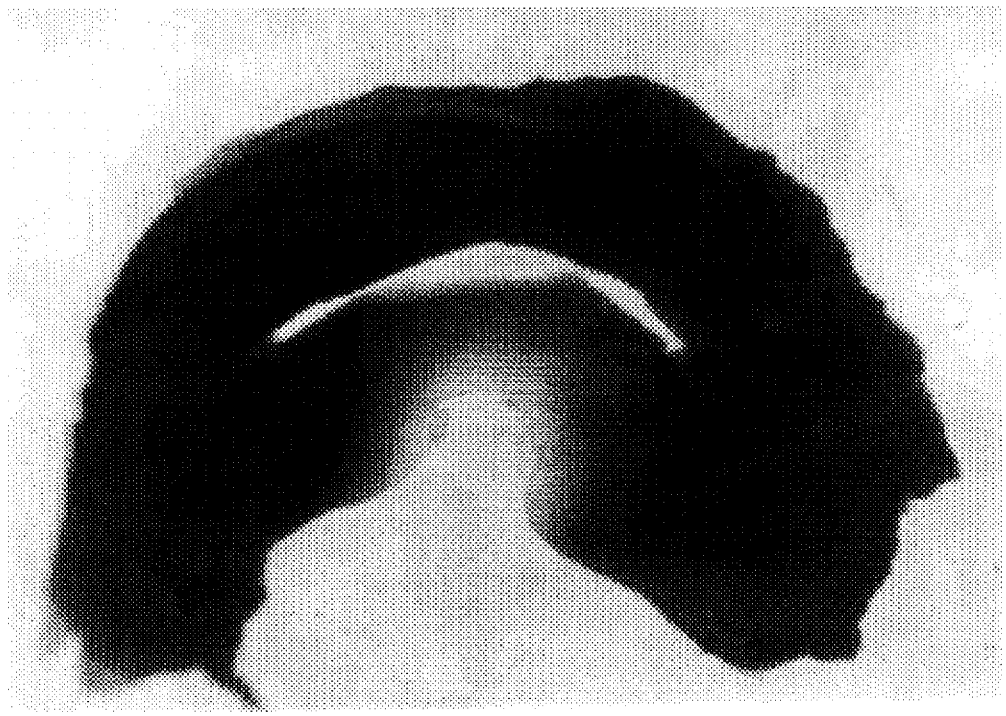
FIG. 6 is a photographic representation of menisci with segmental defects.
Figure 7:
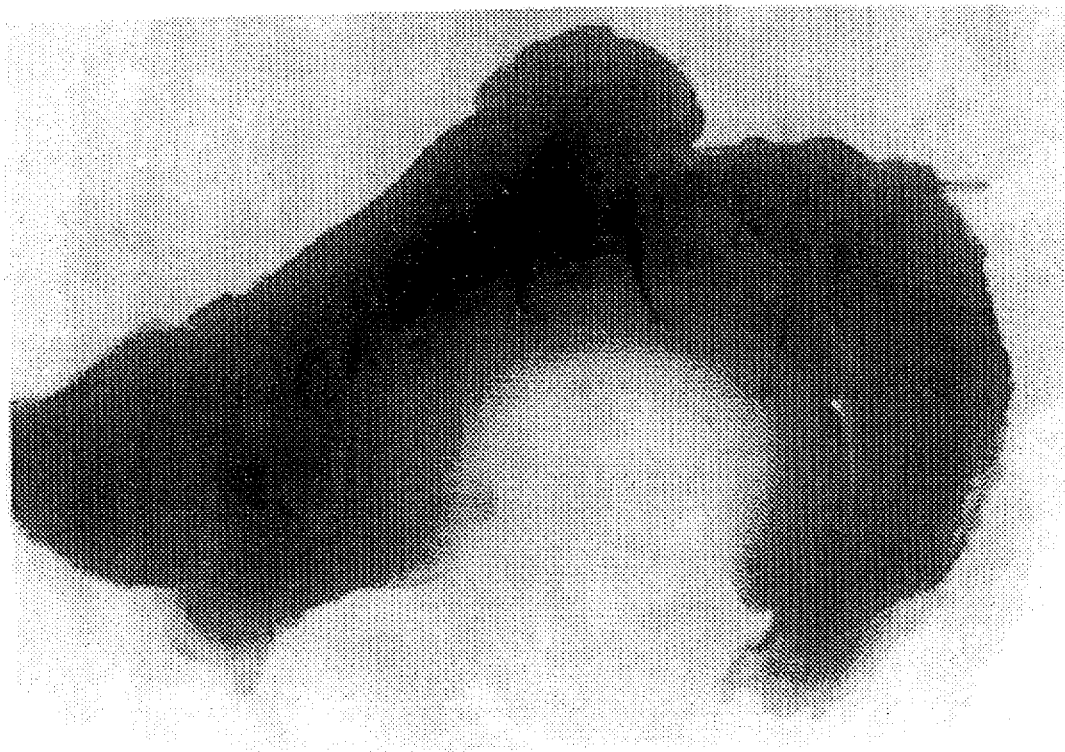
FIG. 7 is a photographic representation of a meniscal augmentation device that has been sutured into a segmental defect of a meniscus.

It has been discovered that a meniscal augmentation device fabricated from biocompatible and bioresorbable fibers can be surgically implanted into a segmental defect of a meniscus so as to provide normal joint motion and strength. The meniscal augmentation device also acts as a scaffold for regenerating meniscal tissue the ingrowth of which is encouraged by the physical characteristics of the implanted device. Such ingrowth results in a composite of the host meniscus and the augmentation device which has an in vivo outer surface contour which is substantially the same as a natural meniscus without a segmental defect.

The fibers of the meniscal augmentation device of the present invention are typically in the form of a dry, porous volume matrix, a portion of which may be crosslinked. In a preferred embodiment, the fibers comprise a natural material, preferably natural polymers, which can provide lubrication as well as mechanical strength. In addition, the porous matrix encourages ingrowth of meniscal fibrochondrocytes, endothelial cells, fibroblasts, and other cells that normally occupy the extracellular matrix as well as synthesize and deposit extracellular matrix components. These fibers include collagen, elastin, reticulin, analogs thereof and mixtures thereof which are generally obtained from animal or human tissue. In some forms of the invention, the fibers may be randomly oriented throughout the matrix. Alternatively, the fibers may assume substantially circumferentially extending or substantially radially extending orientation throughout the meniscal augmentation device. The density of the fibers of the meniscal augmentation device may be uniform or non-uniform throughout the device. In the non-uniform configuration, relatively high densities of fibers may be established at anticipated points of high stress.

In order to encourage ingrowth of meniscal fibrochondrocytes and other types of cells into the porous volume matrix of the present invention while at the same time preserving the mechanical strength and cushioning ability of the device, the density of the meniscal augmentation device can be manipulated. For example, if a relatively great intrafibrillary and interfibrillary space is desired to encourage tissue growth into the matrix, the density of the device can be in the range from about 0.07 to about 0.15 g matrix/cm$^3$, where g/cm$^3$ represents the number of grams in a cubic centimeter of the matrix. Alternatively, if a relatively small intrafibrillary and interfibrillary space is desired to provide mechanical support for the knee joint and improved cushioning, the density of the device be designed to be in the range from about 0.15 to about 0.50 g matrix/cm$^3$. In a preferred embodiment of the present invention, the matrix has a density of about 0.10 to about 0.25 g matrix/cm$^3$ with an intrafibrillary and interfibrillary space of about 8 cm$^3$/g matrix to about 9 cm$^3$/g matrix, which offers an ideal environment for ingrowth of meniscal fibrochondrocytes as well as other cells while maintaining sufficient mechanical strength to support natural meniscal load forces.

The matrix can also include glycosaminoglycan molecules (GAGs) interspersed throughout the fibers. These molecules contain chains of repeating disaccharide units containing an N-acetylated hexosamine and provide lubrication and crosslinks for the meniscal augmentation device. Examples of GAGs that can be used in the present invention include chondroitin 4-sulfate, chondroitin 6-sulfate, keratan sulfate, dermatan sulfate, heparan sulfate, hyaluronic acid, and mixtures thereof as components of the matrix. The GAGs can be uniformly dispersed throughout the meniscal augmentation device as individual molecules, or they can be present in varying amounts in different regions of the device. The matrix can be composed of about 75–100% natural fibers and about 0–25% GAGs by dry weight. These proportions can be constant or variable throughout the matrix.

The temporary stability of the shape of the meniscal augmentation device when in vivo, and the rate of resorption of the fibers (and GAGs if the device contains GAGs), are both attributed to crosslinks between at least a portion of the fibers. In addition, GAGs can directly participate in the formation of covalent crosslinks with the fibers or can interact mechanically with the fibers by entanglement to form stable fiber-GAG complexes. The crosslinking reagents used to form these crosslinks include biocompatible bifunctional reagents. These reagents can interact with amino, carboxyl, or hydroxyl groups on a single molecule to form intramolecular crosslinks. Alternatively, they may interact with amino, carboxyl, or hydroxyl on different molecules or on fibers and GAGs to form intermolecular crosslinks. Useful crosslinking reagents include glutaraldehyde, formaldehyde, biocompatible/bifunctional aldehydes, carbodiimides, hexamethylene diisocyanate, bis-imidates, polyglycerol polyglycidyl ether, glyoxal, and mixtures thereof.

Intermolecular crosslinks can also be established through a dehydrothermal process (heat and vacuum) which results in peptide bond formation between an amino group of lysine or hydroxylysine and a carboxyl group of aspartic acid or glutamic acid. The crosslinked device has a relatively high thermal stability between about 55° C. to 85° C., preferably between 65° C. to 75° C., for sufficient in vivo stability. This may be achieved through manipulation of the crosslinking conditions, including reagent concentration, temperature, pH, and time.

The crosslinked device maintains a sufficient degree of hydrophilicity and elasticity, thereby simulating the properties of a natural meniscus or a portion thereof (i.e., the ability to sustain mechanical stress and to protect and lubricate articular surfaces). In addition the structure provides an ideal environment for cell infiltration and extracellular matrix synthesis and deposition.

The meniscal augmentation device may be constructed mainly of Type I collagen fibers without GAG crosslinks. Type I collagen fibers may be obtained from the Achilles tendons of animals. However, the fibers may also be obtained from animal skin or from the skin or tendons of humans. The tissues are treated with a series of mechanical and chemical means to either totally remove the non-collagenous materials or reduce them to a minimal level. In the preferred processing steps, the tendon or skin is mechanically disintegrated into fine pieces useful for further processing. The disintegration may be achieved by grinding the tissue at liquid nitrogen temperature, or by cutting the tissue into small pieces with a sharp knife. In certain applications, the tendons are mechanically disintegrated along the fiber direction in order to maintain the length of the fibers for mechanical strength.

Salt extraction of tendon at neutral pH removes a small portion of the collagen molecules that are newly synthesized and have not yet been incorporated into the stable fibrils. Salt also removes some glycoproteins and proteoglycans that are associated with collagen through electrostatic interactions. Other salts such as KCl and the like can be used as a substitute for NaCl.

Lipids that are associated with the cell membranes or collagenous matrices may be removed by first extracting with detergents such as Triton X-100, followed by extracting with ether-ethanol mixtures. The concentration of Triton X-100 is usually about 2–4%, but is preferably about 3%. The preferred mixture of ether-ethanol is usually at about a 1:1 ratio (v/v). The period of extraction is usually from 8 hours to 96 hours, preferably from about 24 to 48 hours.

Further extraction may be accomplished by matrix swelling conducted at two extreme pHs. Both acidic and basic swelling weakens the non-covalent intermolecular interactions, thus facilitating the release of non-covalently attached glycoproteins, GAGs, and other non-collagenous molecules through the open pores of the collagenous matrices.

The swelling of matrix at alkaline pH is done by treating the collagen at high pH with $Ca(OH)_2$, NaOH, or the like, for a period of about 8 to 96 hours. Alkali extraction in the presence of triple-helical stabilizing salts such as $(CH_3)_4NCl$, $(NH_4)_2SO_4$, or the like reduces the potential risk of denaturation of the collagen. Alkali treatment dissociates the non-crosslinked glycoproteins and GAGs from the collagen matrices. The alkali also removes the residual lipids through saponification.

The acid swelling may be conducted at a low pH in the presence of acetic acid, HCl, or the like. Like the alkali treatment, the acid swelling removes non-crosslinked glycoproteins and GAGs.

The non-triple helical portions of the molecule (telopeptides) are involved in intermolecular crosslinking formation. They are weak antigens and are susceptible to attack by proteases, such as pepsin, trypsin, and the like. Prolonged digestion with such proteases dissociates the fibrils (fibers) into individual molecules. However, if the digestion process is properly controlled such that maximal telopeptides are removed without complete dissociation, the immunogenic properties of the fibrils can be reduced to a minimal level without compromising the mechanical strength. For example, to isolate molecular collagen, the digestion of skin or tendon with pepsin is usually conducted at an enzyme:collagen ratio of about 1:10 for about 24–96 hours at below room temperature. In comparison, fibrils may be obtained by limited pepsin digestion achieved at a ratio of about 1:100 (enzyme:collagen) for about 24–96 hours at 4° C.

Collagen fibers obtained according to this method are then used to fabricate the meniscal augmentation device of the present invention. However, it must be appreciated that different types of collagen, such as Type II collagen, or collagen obtained from other sources, such as biosynthetically-produced collagen or analogs thereof, can also be used in the construction of the meniscal augmentation device.

The prosthetic meniscal augmentation device may further include an adhesion molecule, or adhesive portion or analog thereof, which is incorporated within the network of fibers. As used herein, an adhesion molecule is one which aids in meniscal tissue regeneration by providing a tacky surface in the device to which cells can stick. Useful adhesion molecules include, but are not limited to, chondronectin, osteonectin, and fibronectin (see e.g., U.S. Pat. Nos. 4,589,881, 4,661,111, and 4,578,079), a portion of which can be conjugated to, for example, chondroitin sulfate, and the like.

Alternatively, or in addition, the prosthetic augmentation device may include growth factors interspersed throughout and incorporated throughout the network of fibers, and which aid in meniscal tissue regeneration. The growth factors include, but are not limited to, transforming growth factor -$\alpha$, transforming growth factor-$\beta$, fibroblast growth factor, epidermal growth factor, platelet derived growth factor, and the like, and analogs of such growth factors having the biological activity of its corresponding natural growth factor. The matrix may also contain more than one type of growth factor in any combination.

The present invention further pertains to a method of fabricating a meniscal augmentation device of the type described above. The method generally includes placing a plurality of fibers (or fibers and GAGs, or fibers and growth factors and/or adhesion factors and/or GAGS), into a mold having a shape defined by the segmental defect in the meniscus which is to be repaired (or defining a shape larger than that of the segmental defect to be repaired), lyophilizing the fibers, and contacting the fibers or the fibers and GAGs with a chemical crosslinking reagent such that the fibers or the fibers and GAGs assume the shape of the mold to obtain a dry, porous volume matrix. The mold may define the outer surface of the device to complement the segmental defect. Alternatively, in cases where the other aspects of the invention, an additional crosslinking step is performed by lyophilizing the chemically crosslinked matrix and then subjecting it to dehydrothermal crosslinking procedures. In cases where the mold defines a shape larger than a specific defect-to-be-repaired, the outer contour of the matrix may be cut so that it complements the defect.

The fibers are placed randomly or oriented in specific directions in, for example, mold forms such as a cylindrical form. For example, the fibers can be placed in the mold in a circumferential orientation by rotating the mold as the fibers are placed therein. Alternatively, the fibers can be oriented radially in the mold by manually painting the fibers in a linear, radially directed pattern. Other components such as GAGs which may participate in the crosslinking reactions, can be mixed in with the fibers in a random or non-random fashion before the structure is subjected to various crosslinking and dehydrating procedures including various chemical and/or dehydrothermal methods. Adhesion molecules or adhesive fragments or analogs thereof, or growth factors or biologically active fragments or analogs thereof, may be incorporated into this structure during processing.

Specific densities and pore sizes can be obtained in various regions of the matrix by compressing the fibers or the fibers and GAGs in the mold prior to the chemical crosslinking step. This may be accomplished by applying pressure to a specific region of the matrix with a piston of a predetermined shape. A preferred pore size range is from about 50 microns to about 500 microns.

By following the processes described in the above examples, a meniscal augmentation device of the invention can be constructed having the characteristics listed below in Table I.

TABLE I

| Physical Characteristics | |
|---|---|
| Inner margin height | 2–10 mm |
| Outer margin height | 4–10 mm |
| density | 0.07–0.05 g/cm$^2$ |
| intra- and interfibrillary space | 3.5–9.5 cm$^3$/g matrix |
| Constituents | |
| fiber (collagen) content | 75–100% |
| GAG content | 0–25% |
| growth factors | 0–1% |
| adhesion molecules | 0–1% |

The present invention further pertains to a method for regenerating meniscal tissue in vivo. This method includes fabricating a meniscal augmentation device by the method described above and implanting the meniscal augmentation device into a segmental defect in the meniscus of a subject. The term "subject" is intended to include living organisms susceptible to meniscal defects, e.g., mammals. Examples of subjects include humans, dogs, cats, horses, cows, goats, rats and mice. One method for surgically implanting the meniscal augmentation device of the present invention is described below in Example 25 and depicted in FIGS. 8–12.

The present invention is further illustrated by the following examples which in no way should be construed as being further limiting. The contents of all cited literature references, issued patents, published patent applications, and co-pending patent applications cited throughout this application are hereby expressly incorporated by reference.

EXAMPLES

1. Preparation of Insoluble Type I Collagen Method 1

(A) Tissue Preparation

Bovine Achilles tendon is obtained from USDA-approved slaughter houses. The preferred age of the animals is between 12–18 months. The tissue is kept cold during the purification process except where specified to minimize bacterial contamination and tissue degradation.

(B) Mechanical Disintegration

The adhering tissues and contaminants such as hair, fat and foreign materials of carefully selected tendons are first scraped off mechanically. The tendons are then sliced perpendicular to the tendon axis using a commercial stainless steel meat slicer into thin slices of thickness 0.5 mm to 1.0 mm. The tendons may be sliced along the tendon axis to produce long fibers.

(C) Water Extraction

The sliced tendons are extracted twice in two volumes of pyrogen-free distilled water for a total of 4 to 8 hours at 22° C. with agitation to remove the blood and water soluble proteins.

(D) Lipid Extraction

The sliced tendons are extracted twice each with four volumes of isopropanol for a total of 24 hours with agitation to remove the lipids. The isopropanol extracted tendons are washed twice each with 10 volumes of pyrogen-free distilled water for a total of 2 to 4 hours at 22° C. to remove the isopropanol.

(E) Sodium Chloride Extraction

The sliced tendons are extracted in 10 volumes of pre-filtered (0.2 μm) 5% sodium chloride solution for about 20 hours at 22° C. with agitation to remove the salt soluble non-collagenous materials. The salt extracted tendons are washed in 10 volumes of pyrogen-free distilled water to remove the salt.

(F) Sodium Hydroxide Extraction

The alkaline extraction removes the alkaline sensitive non-collagenous materials including residual lipids. The alkaline extraction of the tendon is carried out at a pH above 13 in the presence of a triple helical stabilizing salt to prevent excessive swelling and protein denaturation. Tendons are extracted in 5 volumes of 1.0M sodium hydroxide (NaOH) solution in the presence of 1.1M sodium sulfate ($Na_2SO_4$) as a structure stabilizing salt for 24 hours at 22° C. with agitation. The alkaline extracted tendons are first neutralized to about pH 5.0 with 0.15M sulfuric acid in the presence of 1.1M sodium sulfate to minimize the swelling of the tendon, followed by four times of rinse in 10 volumes of pyrogen free water pre-adjusted to pH 5.0 to remove the salt.

(G) Freeze Drying

The purified tendon slices are freeze dried in a Virtis freeze dryer and stored dry until use.

2. Preparation of Insoluble Type I Collagen Method 2

(A) Tissue

Bovine, porcine, or sheep Achilles tendon is obtained from USDA-approved slaughter houses. The preferred age of the animals is between 12–18 months.

(B) Mechanical Disintegration

The adhering tissues of carefully selected tendons are first scraped off mechanically. The tendons are then minced or cut into fine pieces and washed in excess quantities (10 volumes) of cold water to remove residual blood proteins and water soluble materials.

(C) Salt Extraction

The washed tendons are extracted in ten volumes of 5% NaCl, 0.01M Tris-HCl, pH 7.4, for 24 (±4) hours to remove salt soluble materials. The salt extracted tendons are repeatedly washed in about 10 volumes of water to remove the salt.

(D) Lipid Extraction

The material is extracted in 3% Triton X-100 for 24 (±2) hours. The detergent is removed by extensive washing with water. The material is then extracted in 3–4 volumes of ether-ethanol (1:1 vol/vol) for 24 (±2) hours to further minimize the lipid content. The lipid extracted material is extensively washed in water to remove the ether and ethanol.

(E) Matrix Swelling

The material is then subjected to two extreme pH extractions to remove non-collagenous materials. Alkaline extraction is conducted with 3–4 volumes of 0.2M NaOH at pH 12.5–13.5 at room temperature in the presence of 1.0M $(CH_3)_4NCl$ for 24 (±22) hours with mild agitation.

Following alkaline extraction, the pH is neutralized with HCl and the material is washed with water. The pH is then adjusted to 2.5–3.0 by adding concentrated acetic acid to a final concentration of 0.5M. The acid extraction is continued for 24 (±2) hours with agitation.

(F) Limited Proteolytic Digestion

The acid swollen material is then subjected to a limited proteolytic digestion with pepsin (enzyme:collagen is 1:100) for 24 (±2) hours. The pepsin and telopeptides are removed through dialysis.

The swollen fibrillar material is then coacervated by adjusting the pH to its isoionic point with 1M NaOH or HCl or by adjusting the ionic strength to 0.7 with NaCl. The aggregated collagen fibers are harvested by filtration, and filtered material extensively washed with cold buffered solution. The highly purified type I collagen may be stored (−20° to −40° C.) until used.

3. Preparation of Soluble Type I Collagen

Tissue preparation (A), mechanical disintegration (B), and water extraction (C), are performed as described in Example 1.

(D) Pepsin Digestion

The tendon slices are swollen in 10 volumes of 0.07M lactic acid. Pepsin at a ratio of 1:10 enzyme:tendon (w/w) is then added to the tendon and the tissue is digested for about 24 hours at 4° C. The digested tendons are filtered with a mesh screen filter and supernatant is collected and stored in a refrigerator. The insoluble residues are reextracted with pepsin and the supernatant again is collected. The supernatants are combined and filtered through 60 mesh and 200 mesh stainless steel screens.

(E) Precipitation

NaCl crystals are slowly added to the filtered supernatant, while stirring, to a final concentration of 1.0M. Type I collagen slowly precipitates out from the solution. The precipitate is centrifuged and collected.

(F) Purification

The precipitate is redissolved in 10 volumes of 0.03M lactic acid and reprecipitated with 1M NaCl. The precipitate is again centrifuged and precipitate collected. Finally, the precipitate is redissolved in 1 volume of 0.03M lactic acid and dialyzed against distilled water to remove the acid. The dialyzed soluble Type I collagen is freeze dried and stored dry until use.

4. Preparation of Insoluble Type II Collagen

(A) Tissue

Bovine knee joint is obtained from USDA-approved slaughter houses. The articular cartilage of the femoral condyles and tibia plateaus are sliced off into thin slices using a sharp knife. The sliced articular cartilages are extensively washed in distilled water and freeze dried.

(B) Mechanical Disintegration

The dry cartilage slices are shredded in a grinder or in a stainless steel Waring blender to reduce the tissue size for extraction.

Lipid extraction (C) and sodium chloride extraction (D) are performed as described in Example 1 above.

(E) Guanidine-Hydrochloride Extraction

The cartilage tissues are extracted twice each with 10 volumes of 4M Guanidine-HCl for 24 hours at 4° C. with stirring. The extracted cartilage tissues are washed with 10 volumes of distilled water to remove the guanidine-HCl.

Sodium hydroxide extraction (F) and freeze drying of the insoluble cartilage Type II collagen (G) are performed as described in Example 1 above.

5. Preparation of Soluble Type II Collagen

Tissue preparation (A) and mechanical disintegration (B) are performed as described above in Example 4.

(C) Triton X-100 Extraction

The cartilage tissues are extracted in 10 volumes of 1% Triton X-100 and 2M NaCl for 24 hours with stirring at 4° C.

(D) Guanidine-Hydrochloride Extraction

The cartilage tissues are extracted with 10 volumes of 4M guanidine-HCl for 24 hours at 4° C. and the extractant is discarded. The insoluble residues are washed with 10 volumes of distilled water for 24 hours to remove the salt and guanidine-HCl.

(E) Pepsin Digestion

The cartilage tissues are first swollen in 0.07M lactic acid at pH 2.5 to pH 3.0. The pepsin at a ratio of 1:10 w/w enzyme:cartilage is then added and the tissue is digested for 24 hours at 4° C. The digested tissue is filtered with a No. 30 mesh screen filter and the supernatant is collected and stored in cold. The insoluble residues are digested again with pepsin and the supernatant is combined with the first extraction.

Precipitation of cartilage Type II collagen and purification of Type II collagen are performed as described in Example 2 above.

6. Preparation of Insoluble Type I Collagen Dispersion

Approximately 100 g of purified collagen from Example 1 is added to 14 liters of 0.07M lactic acid in a stainless steel vessel to swell the collagen. The pH of the swollen collagen should be between 2.5 to about 3.0. The swollen collagen is homogenized in an in-line Silverson Homogenizer (East Longmeadow, Mass.). The homogenized collagen dispersion is filtered through a 30 mesh stainless steel filter to remove the non-homogenized particles and to obtain a uniform dispersion for the device fabrication.

7. Preparation of Insoluble Type II Collagen Dispersion

Same as Example 6 except Type II collagen from Example 4 is substituted for Type I collagen.

8. Preparation of Insoluble Type I Collagen-GAG Dispersion

Approximately 1.3 g hyaluronic acid and 1.3 g chondroitin sulfate are dissolved in 14 liters 0.07M lactic acid in a stainless steel vessel. About 100 g of the purified Type I collagen from Example 1 is then added to the GAG solution to swell the collagen for a minimum of four hours. The swollen collagen-GAG material is homogenized in an in-line Silverson Homogenizer (East Longmeadow, Mass.). The homogenized collagen-GAG dispersion is filtered through a 30 mesh stainless steel filter to remove the non-homogenized particles and to obtain a uniform dispersion for the device fabrication.

9. Preparation of Insoluble Type I Collagen-TGF Dispersion

Approximately 10 µg TGF-α or TGF-β (Gibco BRL, Grand Island, N.Y.) is dissolved in 14 liters 0.07M lactic acid in a stainless steel vessel. About 10 g of the purified Type I collagen from Example 1 is then added to the TGF-β solution to swell the collagen for a minimum of four hours. The swollen collagen-TGF-β material is homogenized in an in-line Silverson Homogenizer (East Longmeadow, Mass.). The homogenized collagen-TGF-β dispersion is filtered through a 30 mesh stainless steel filter to remove the non-homogenized particles and to obtain a uniform dispersion for the device fabrication.

10. Preparation of Insoluble Type I and Type II Collagen Dispersion

Approximately 50 g Type I collagen (from Example 1) and 50 g of Type II collagen (from Example 4) are swollen in 14 liters of 0.07M lactic acid solution. The swollen collagens are then homogenized in an in-line Silverson Homogenizer (East Longmeadow, Mass.). The homogenized Type I-Type II (1:1, W/W) collagen mixture is filtered through a 30 mesh stainless steel filter to remove the large particles. The dispersed Type I-Type II collagen mixture in now ready for device fabrication.

11. Preparation of insoluble Type I Collagen—Soluble Type II Collagen Dispersion Approximately 50 g of soluble Type II collagen (from Example 4) is dissolved in 14 liters of 0.07M lactic acid. 50 g insoluble Type I collagen (from Example) is then added to the Type II collagen solution to swell the Type I collagen. The swollen Type I collagen homogenized and filtered as in Example 5. The dispersed Type I-Type II collagen (1:1, W/W) mixture is now ready for device fabrication.

12. Device I Fabrication (A) Approximately 700 g of a Type I collagen dispersion (prepared as described in Example 6) is weighed into a 2 liter vacuum flask. Approximately 120 ml 0.6% ammonium hydroxide is added to the dispersion to coacervate the collagen. About 80 ml 20% NaCl is then added to the coacervated fibers to further reduce the solution imbibition between the fibers.

(B) The fully coacervated fibers are dehydrated to about 70 g to 80 g in a perforated mesh basket to remove the excess solution from the fibers.

(C) The partially dehydrated collagen fibers are inserted into a mold of specified dimension related to the dimensions of the defect to be remedied. Further dehydration is ongoing in the mold using a constant (between 300 grams to 700 grams) weight to slowly remove the water from the fibers, yet maintaining the same density throughout. This slow dehydration process lasts for about 24 hours until the desired dimension (about 8 mm in thickness) is reached.

(D) The dehydrated collagen matrix is further shaped to the desired form figure.

(E) The dehydrated collagen fibers are frozen at −20° C. for at least 4 hours before freeze drying in a Virtis freeze dryer.

(F) The frozen collagen fibers are first dried at −10° C. for 48 to 72 hours, followed by drying at 20° C. for 16 to 24 hours at a vacuum of 400 millibar.

(G) The freeze dried matrices are subjected to a formaldehyde crosslinking procedure. The matrices are crosslinked for 40 hours in a closed chamber of formaldehyde vapor generated from a 2% formaldehyde solution at 22° C. The crosslinked matrices are vented extensively to remove the non-bounded formaldehyde.

(H) The matrices are then subjected to a heat and vacuum treatment to further crosslink the matrices.

(I) The matrices are cut to the shape of the segmental defect of the meniscus to be repaired. The cut matrices are extensively rinsed in pyrogen free distilled water to remove the residual salts and formaldehyde to the extent that the matrices are biocompatible in vitro and in vivo.

(J) The rinsed matrices are dried under a hepafilter and are packaged and sterilized.

13. Device II Fabrication

The procedure for fabricating Device II is identical to that described in Example 12, except that approximately 700 g of a Type II collagen dispersion (prepared as described in Example 5) are used.

14. Device III Fabrication

The procedure for fabricating Device III is identical to that described in Example 12, except that approximately 700 g of a Type II collagen dispersion (prepared as described in Example 7) is used.

15. Device IV Fabrication

The procedure for fabricating Device IV is identical to that described in Example 12, except that approximately 700 g of a Type II collage-GAG dispersion (prepared as described in Example 8) are used.

16. Device V Fabrication

The procedure for fabricating Device V is identical to that described in Example 12, except that approximately 700 g of a Type I collagen-TGF-β dispersion (prepared as described in Example 9) is used.

17. Device VI Fabrication (A) The collagen content of the highly purified type I collagen fibrils from Example 2 is determined either by gravimetric methods or by determining the hydroxyproline content assuming a 13.5% by weight of hydroxyproline in Type I collagen. The amount of purified material needed to fabricate a given density of a meniscal augmentation device is then determined and weighed.

(B) A solution of fibrillar collagen is fit into a mold of specified dimensions, e.g., according to the exemplary meniscal augmentation devices described above. Collagen fibers are laid down in random manner or in an oriented manner. In the oriented manner, circumferential orientation of the fibers is produced by rotation of the piston about its principal axis as the material is compressed in the mold; radial orientation is produced by manual painting of the collagen fibers in a linear, radially directed fashion.

(C) The fibers are frozen at −20° C., turned out of the mold, and thawed at room temperature.

(D) The fibers are then resuspended in phosphate buffered saline, put back into the mold in the desired orientations(s), and compressed with the piston.

(E) The compressed fibers are then refrozen −20° C. and then thawed at room temperature.

(F) The resulting structure is crosslinked by soaking in a 0.2% glutaraldehyde solution, pH 7.6 for 24 (±0.5) hours. Each glutaraldehyde-crosslinked meniscal augmentation device is subsequently rinsed repeatedly in 500 ml of phosphate buffered saline (PBS) solution, pH 7.4, for 4, 8, 24, and 48 hours.

(G) The rinsed matrix is then lyophilized.

18. Device VII Fabrication

Steps (A)–(G) are the same as in Example 17.

(H) The lyophilized matrix is subject to dehydrothermal crosslinking by vacuum and heat. The vacuum is first applied to reduce the residual water content to a minimal level (some structural water, about 3%, may still be associated with collagen triple-helix as part of the structure stabilizing factor). The heat is increasing in steps to 100° C. under vacuum for 24 (±2) hours.

19. Device VIII Fabrication

Step (A) is the same as in Example 17.

(B) The collagen material is dispersed in 0.01M HCl solution at pH 2–2.5. Predetermined amounts of various GAGs are weighed an dissolved in water. For example, for a given density of 0.25 g/cm, the collagen content will be 0.244 g, the hyaluronic acid content will be 0.003 g, and the chondroitin sulfate content will be 0.003 for a 2.5% GAG content. The GAG solution is mixed in with the collagen solution and placed in the mold in the desired orientation as described in Example 12.

Steps (C)–(G) are the same as in Example 17.

20. Device IX Fabrication

Steps (A)–(C) are the same as in Example 17.

Step (D) is the same as in Example 17 except that the fibers laid down are not compressed.

Steps (E)–(G) are the same as in Example 17.

21. Device X Fabrication

Steps (A)–(E) are the same as in Example 17.

(F) The molded collagen is crosslinked in 5% polyglycerol polyglycidyl ether in 50% ethanol and 0.1M $Na_2CO_3$ at pH 10.0 for 24 (±2) hours. The crosslinked device is rinsed for 4, 8, 24 and 48 hours, each with 500 ml of PBS, pH 7.4.

Step (b) is the same as in Example 17.

22. Device XI Fabrication

Steps (A)–(E) are the same as in Example 17.

(F) The molded collagen is crosslinked in the presence of 10 ethyl-3-(3-dimethylaminopropyl) carbodiimide (10 mg/g matrix) in 0.9% NaCl, pH 4.7 at room temperature for 24 (±2) hours. The addition of carbodiimide is made every 3–4 hours, and the pH is adjusted to 4.7 after each addition of carbodiimide.

Step (G) is the same as in Example 17.

23. in vitro Testing

In vitro testing was performed to determine the ability of the meniscal augmentation device to function and/or to serve as a regeneration template for normal meniscal tissues.

Menisci were aseptically harvested from mature dogs, trimmed of all adherent tissue, and placed into Gey's balanced saline solution. Each meniscus was bisected in the coronal plane and 3 mm full-thickness circular defects were made in each meniscal half. The defects were filled with a 3 mm diameter plug of a collagen or a collagen-GAG meniscal augmentation device. The menisci were placed in six well culture plates containing 6 ml Dulbecco's modified Eagle's medium supplemented with 10% fetal bovine serum, sodium ascorbate, and 0.1% penicillin/streptomycin. Cultures were maintained at 37° C. in a humidified atmosphere of 10% $CO_2$/90% air, fed three times per week, and placed in fresh culture wells every week to prevent the formation of explant cell cultures. At intervals of one, four, and six weeks after initiation of culture, three menisci from each group were removed, fixed and evaluated with serial sections and staining.

The results demonstrate increasing cellular migration and superficial invasion over time. There was no apparent toxicity from the implant material. The migrating cells were more fusiform and elongated that native meniscal fibrochondrocytes. The depth of the cellular penetration into the scaffold appeared to be limited by the density of the meniscal augmentation device.

The meniscal augmentation devices manufactured as described above were also tested according to the following procedures.

(A) Suture Pullout Test

The purpose of the suture pullout test is to ascertain that the suture pullout strength of the hydrated matrix exceeds the strength requirement for surgical implantation. The suture pullout test is determined by passing a 2–0 Maxon suture (Davis & Geck, Danbury, Conn.), attached to a C-9 27 mm needle through the product 3 mm from the outer edge of a pre-hydrated sample. A knot is tied and the loop is attached to the hook of a force gauge (Shimpo America Corp., Lincolnwood, Ill.). The sample is pulled by hand until the suture pulls out or until the force is greater than 3 lbs.

The suture pullout force is greater than 3 lbs. This strength meets the strength requirement for surgical implantation.

(B) Swelling Test

The purpose of the exemplary swelling test is to measure the extent of hydration, which is related to the density of the matrix. The swelling index is defined as the weight of solution uptake per weight of the dry collagen matrix. The swelling index is determined by first measuring the dry weight of the sample and then placing the sample in distilled water for 20 minutes. The excess water is removed from the sample by tapping against the glass wall of the beaker. The wet weight is then measured.

The swelling index is 4.3 g/g matrix. This swelling in consistent with density requirement for pore structure and tissue ingrowth.

(C) Shrinkage Temperature

The purpose of the shrinkage temperature test is to ascertain that the extent of crosslinking is sufficient for in vivo stability and tissue growth as measured by the hydrothermal shrinkage temperature of the matrix. A slice having the dimensions 0.7 cm×1.5 cm×0.2 cm is attached to the shrinkage temperature apparatus. One end of the collagen sample is clamped at a fixed point. The other end of the sample is then attached to a small weight through a pulley to maintain a constant tension. The sample is equilibrated in a beaker of 0.01M phosphate buffered saline, pH 7.4. The solution is heated at a rate of 1° C. per minute. The length of the sample in terms of the deflected angle is continuously recorded manually. The shrinkage temperature of the matrix is defined as the temperature at which the length starts to change (onset point of angle deflection).

The crosslinked matrix has an average thermal shrinkage temperature of 67° C. This temperature has been found in dog studies to be sufficient to maintain in vivo stability for tissue growth.

(D) Density

The purpose of the density test is to ensure that the density is within the design guidelines for pore structure for tissue ingrowth. The dimensions of a matrix are first measured with an electric caliper to within 0.2 mm. The volume is then calculated. The matrix is then dried in an oven for 4 hours at 100° C. The dry matrix is weighed to within 0.2 mg accuracy and the density is calculated in g/cm$^3$.

The matrix has an average density of 0.20 g matrix/cm$^3$. This density has a interstitial (interfibrillar) volume of 0.86 cm$^3$ per 1 cm$^3$ total matrix for tissue ingrowth.

(E) Permeability

The purpose of the permeability test is to ascertain the permeability of the matrix to macromolecules for nutrient supply. Random samples are cut into pieces having the dimensions approximately 1.0 cm×0.7 cm×0.5 cm. Each piece is weighed dry and then immersed in 100 ml of 1% bovine serum albumin (BSA) (Sigma Chemical Co., St. Louis, Mo.) for 5 hours. The wet weight is then obtained. The BSA in the matrix is extracted with 100 ml of 0.9% NaCl for 20 hours. The concentration of the BSA in the extractant is then measured according to the procedure based on the method of Bradford (*Anal. Biochem.* (1976) 72:248). Briefly, the procedure consists of reacting 0.5 ml of the extractant with 0.5 ml of Coomassie Plus protein reagent. Standards are prepared using pre-dried BSA. The absorbance of the developed blue color is measured at a wavelength of 595 nm using a spectrophotometer (Perkin Elmer Corp., Norwalk, Conn.).

The interstitial (excluding the intrafibrillar) space within the matrix is completely permeable to BSA, which is consistent with the design criteria.

(F) Pore Structure

The purpose of the pore structure evaluation is to assure that the matrix is sufficiently porous for cellular ingrowth. The pore structure of the matrix is evaluated by examining scanning electron micrographs (SEMs) (Structure Probe, Inc., Metuchen, N.J.) of representative sections of the matrix.

The SEMs show that the pore sizes are in the range of from about 50 microns to about 500 microns of irregular shapes. This range of pore size is sufficient for cellular growth.

24. Surgical Implantation Technique and Cadaveric Testing

Figure 8:
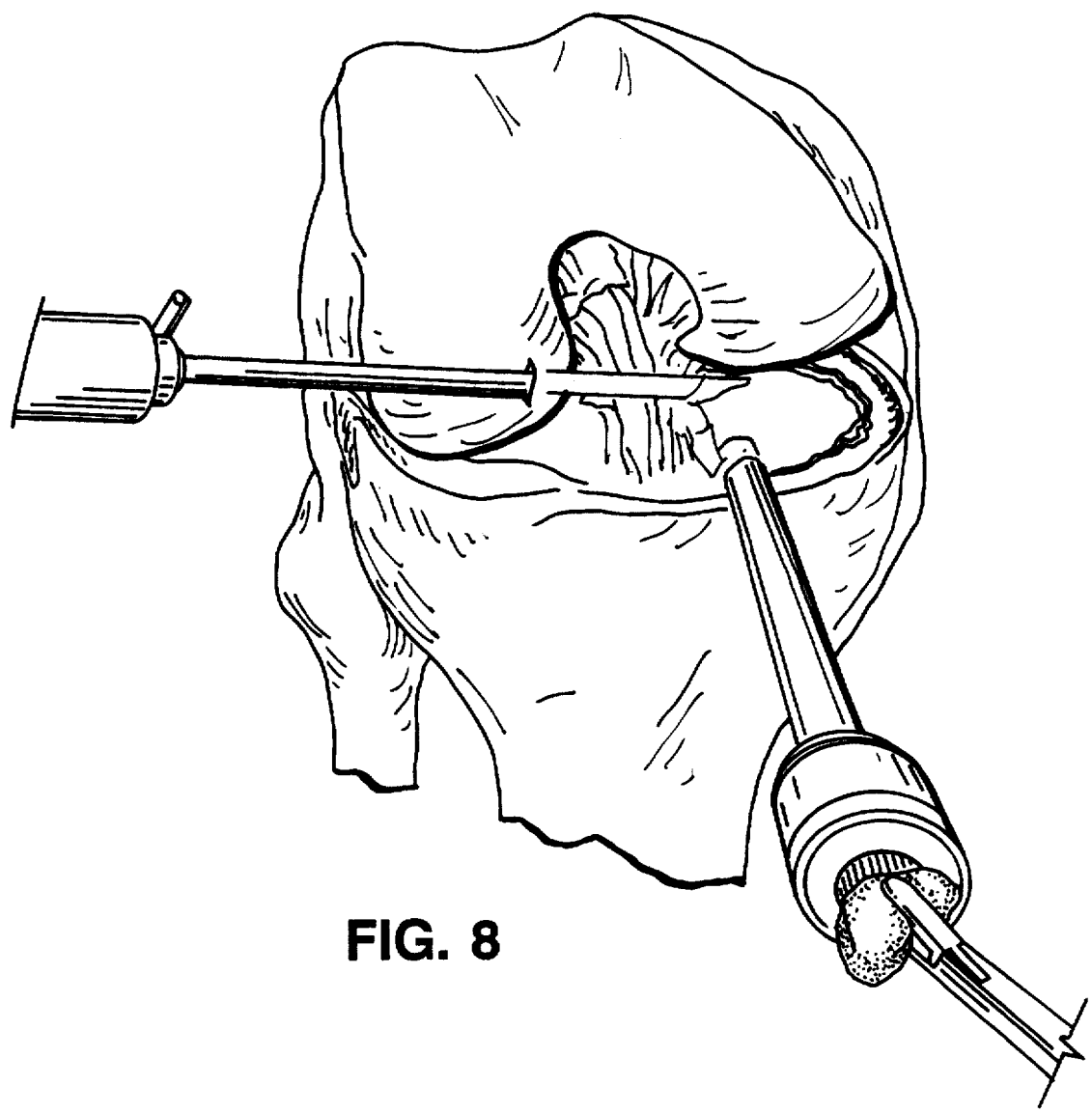
FIG. 8 is a diagrammatic representation of surgically implanting a meniscal augmentation device into a segmental defect in the meniscus.
Figure 9:
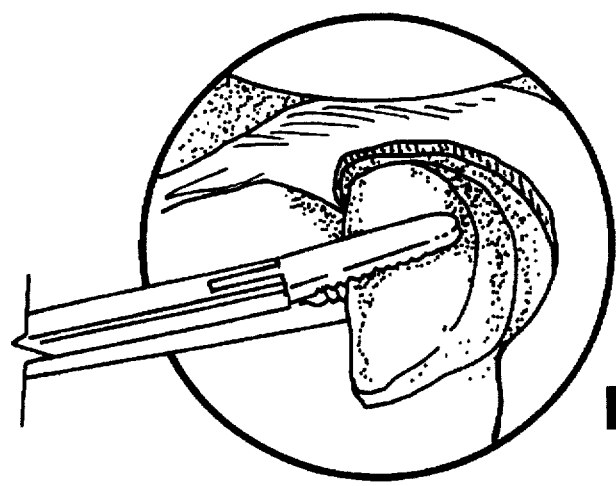
FIG. 9 is a diagrammatic representation of a meniscal augmentation device being placed into a segmental defect in the meniscus.

A meniscal augmentation device containing Type I collagen and GAGs is evaluated in seventy human cadaveric implantations. The devices are implanted into both horizontal cleavage tears and segmental defects. All knees are approached by standard arthroscopic portals. For medial meniscal tears, the arthroscope is placed in the mid lateral patella portal and instrumentation through the anterior medial portal as seen in FIG. 8. While preserving the stable portions of the meniscus, the torn and frayed portions of the meniscus are removed with arthroscopic biters and shavers.

Figure 10:
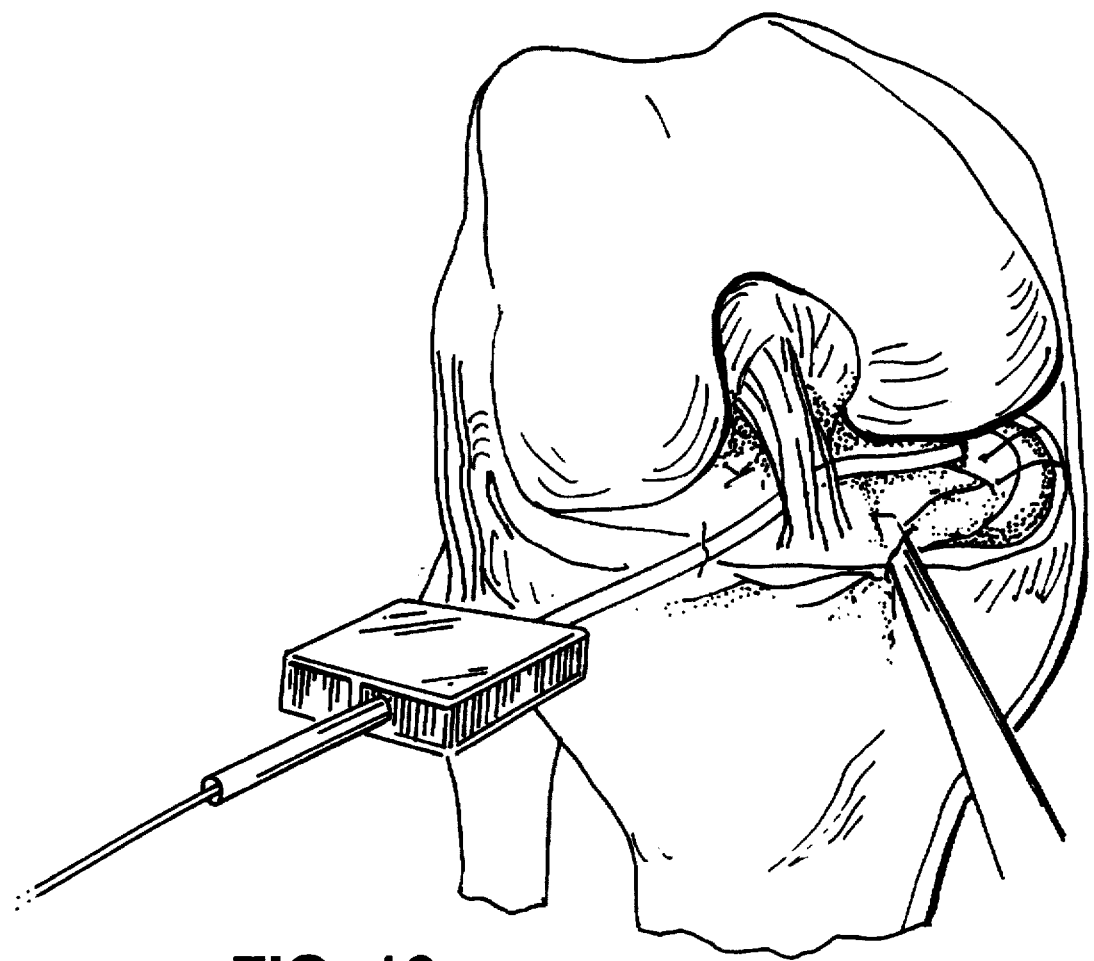
FIG. 10 is a diagrammatic representation of a meniscal augmentation device being sutured into the meniscal cartilage.
Figure 11:
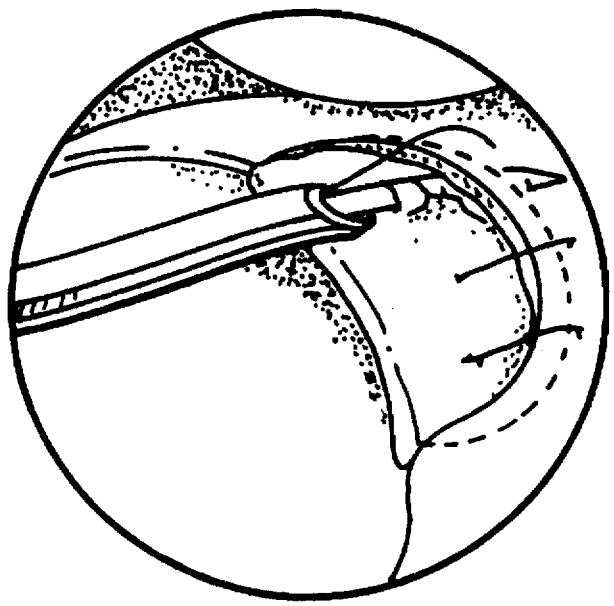
FIG. 11 is a diagrammatic representation of the final suturing to secure a meniscal augmentation device into the native meniscus.
Figure 12:
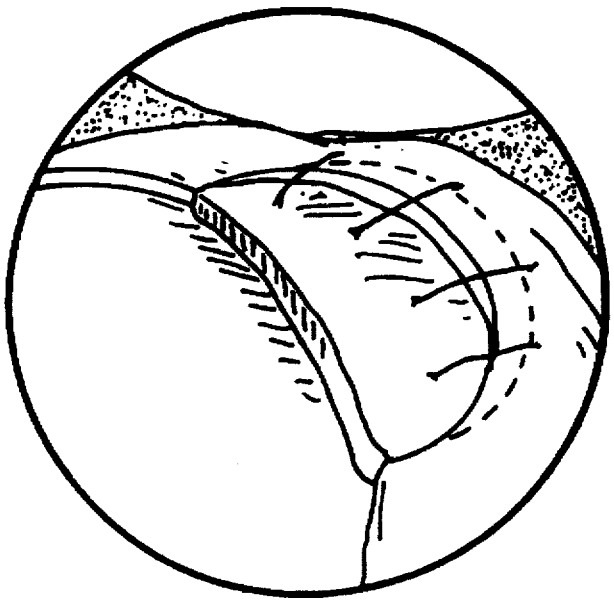
FIG. 12 is a diagrammatic representation of a meniscal augmentation device, as sewn into a native meniscus.

A calibrated probe is then placed along the meniscal defect to obtain measurements of the defect. The probe is then laid upon the meniscal augmentation device and the device trimmed to match the defect. The trimmed portion of the meniscal augmentation device is then grasped with a specially modified arthroscopic grasper and inserted into the segment. While still within the grasper, the device is sutured in place by passing ten inch 2-0 PDS sutures down the bore of the grasper, through the meniscal augmentation device and then through the native meniscus. The sutures are tied directly over the capsule beneath the skin. Additional sutures are placed as shown in FIGS. 10 and 11 to further secure the implant to the meniscal rim. The final appearance of the sutured meniscal augmentation device is shown in FIG. 11.

The knees are flexed and extended through the full range of motion. Despite significant swelling of the device, molding uniformly occurs to match the shape of the opposing articular cartilage and femoral condyle.

Sequential 3D MRI images are obtained in several knees documenting stable placement of the implant, and appropriate excursion on the tibial plateau from 0° to 120° of flexion.

25. in vivo Testing

In vivo testing was performed to determine the ability of the meniscal augmentation device to function and/or to serve as a regeneration template for normal meniscal tissues.

Ten patients underwent surgical implantation of a meniscal augmentation device containing Type I collagen and GAGs. The study was performed as an FDA approved feasiblitiy study, and all patients met rigid criteria including significant loss or irreparable injury to the medial meniscal cartilage. After implantation, clinical follow up evaluations were performed including a customized knee evaluation form, standard and 3D MRI measurements on implant size and location, and a second arthroscopical examination. The implant was observed arthroscopically three months post-implantation. Clinical, gross, radiographic, and histologic evaluations are being done.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method for fabricating a meniscal augmentation device having an in vivo shape of a segmental defect in a meniscus, comprising:

(a) placing a plurality of biocompatible and bioresorbable fibers into a mold, the fibers including natural polymers, analogs of natural polymers, or mixtures of natural polymers;

(b) lyophilizing the molded fibers to produce a dry and porous matrix;

(c) contacting the fibers with a chemical crosslinking agent such that the fibers assume the shape of the mold; and (d) during step (a) or after step (c), shaping the outer surface of said device to be substantially complementary to that of the segmental defect in the meniscus, thereby establishing a dry, porous volume matrix having pores the diameter of which range in size from about 50 microns to about 500 microns, the matrix, when implanted into a knee joint, forming a biocompatible and an at least partially bioresorbable scaffold for ingrowth of meniscal fibrochondrocytes and for supporting natural meniscal load forces, and whereby the in vivo outer surface of the composite of said scaffold and said meniscus is substantially the same as a natural meniscus without a segmental defect.

2. A meniscal augmentation device produced by the method of claim 1.

3. The method of claim 1 wherein the natural polymers are selected from the group of polymers derived from humans and non-human animals.

4. The method of claim 3 wherein the human-derived and non-human animal-derived polymers are selected from the group consisting of collagen, elastin, reticulin, cellulose, analogs thereof, and mixtures thereof.

5. The method of claim 1 wherein (a) further comprises placing a plurality of glycosaminoglycan molecules into the mold.

6. The method of claim 5 wherein the glycosaminoglycan molecules are selected from the group consisting of chondroitin 4-sulfate, chondroitin 6-sulfate, keratan sulfate, dermatan sulfate, heparan sulfate, heparin, hyaluronic acid, and mixtures thereof.

7. The method of claim 1 wherein placing step (a) further comprises orienting the fibers in a desired pattern in the mold.

8. The method of claim 1 wherein the chemical crosslinking agent is selected from the group of crosslinking agents consisting of glutaraldehyde, formaldehyde, biocompatible bifunctional aldehydes, carbodiimides, hexamethylene diisocyanate, bis-imidates, polyglycerol polyglycidyl ether, glyoxal, and mixtures thereof.

9. The method of claim 9 wherein in stem (a) a growth hormone is also placed into the mold.

10. The method of claim 9 wherein the growth factor is transforming growth factor-α, transforming growth factor-β, fibroblast growth factor, epidermal growth factor, platelet derived growth factor, or combinations thereof.

11. The method of claim 11 wherein in step (a) an adhesion factor is also placed into the mold.

12. The method of claim 11 wherein the adhesion molecule is fibronectin, chondronectin, osteonectin, or combinations thereof.

* * * * *